(12) United States Patent
Fisk et al.

(10) Patent No.: US 7,052,611 B2
(45) Date of Patent: May 30, 2006

(54) DEVICE FOR SOLID PHASE EXTRACTION AND METHOD FOR PURIFYING SAMPLES PRIOR TO ANALYSIS

(75) Inventors: Raymond P. Fisk, Norton, MA (US); Pamela Carmen Iraneta, Brighton, MA (US); Yuri Tuvim, Gloucester, MA (US); Edouard S. P. Bouvier, Stow, MA (US); Jonathan Belanger, Whitinsville, MA (US); Martin Gilar, Franklin, MA (US)

(73) Assignee: Waters Investments Limited, New Castle, DE (US)

( * ) Notice: Subject to any disclaimer, the term of this patent is extended or adjusted under 35 U.S.C. 154(b) by 194 days.

(21) Appl. No.: 10/785,754

(22) Filed: Feb. 24, 2004

(65) Prior Publication Data

US 2004/0166589 A1   Aug. 26, 2004

Related U.S. Application Data

(62) Division of application No. 10/100,762, filed on Mar. 19, 2002, now Pat. No. 6,723,236.

(51) Int. Cl.
*B01D 15/08* (2006.01)
(52) U.S. Cl. .................... 210/656; 210/198.2
(58) Field of Classification Search ............... 210/635, 210/656, 659, 198.2; 422/70; 96/101
See application file for complete search history.

(56) References Cited

U.S. PATENT DOCUMENTS

| | | | | |
|---|---|---|---|---|
| 2,561,339 A | | 7/1951 | Chediak | 23/253 |
| 3,478,886 A | * | 11/1969 | Hornbeck | 210/198.2 |
| 4,211,658 A | | 7/1980 | McDonald | 210/198.2 |
| RE30,562 E | | 3/1981 | Park | 435/296 |
| 4,304,865 A | | 12/1981 | O'Brien et al. | 435/240 |
| 4,309,286 A | * | 1/1982 | Lenihan et al. | 210/198.2 |
| 4,551,251 A | * | 11/1985 | Kolobow et al. | 210/635 |
| 4,554,071 A | * | 11/1985 | Ruijten et al. | 210/198.2 |
| 4,734,262 A | | 3/1988 | Bagshawe | 422/101 |
| 4,787,971 A | * | 11/1988 | Donald | 210/198.2 |
| 4,810,381 A | | 3/1989 | Hagen | 210/657 |
| 4,824,560 A | | 4/1989 | Alspector | 209/208 |
| 4,863,592 A | * | 9/1989 | Allington et al. | 210/96.1 |
| 4,902,481 A | | 2/1990 | Clark et al. | 422/101 |
| 4,956,150 A | | 9/1990 | Henry | 422/102 |
| 5,037,544 A | * | 8/1991 | Snyder | 210/198.2 |

(Continued)

FOREIGN PATENT DOCUMENTS

EP  1110610  6/2001  ................ 422/102

OTHER PUBLICATIONS

Snyder, Introduction to Modern Liquid Chromatography, John Wiley & Sons, 1979, pp. 204-206.*

(Continued)

*Primary Examiner*—Ernest G. Therkorn
(74) *Attorney, Agent, or Firm*—Anthony J. Janiuk

(57) ABSTRACT

A solid phase extraction (SPE) device having a reservoir with an opening; a well comprising an internally tapered wall, the well having a wider interior diameter at an end closest to the opening than at an exit spout; a first filter within the well; a bed of sorbent particles within the well below the first filter; and a second filter having a diameter smaller than the first filter within the well below the bed of sorbent particles and above the exit spout is provided. A method of performing SPE using the device is also provided.

8 Claims, 4 Drawing Sheets

U.S. PATENT DOCUMENTS

| | | | |
|---|---|---|---|
| 5,395,521 A | 3/1995 | Jagadeeswaran | 210/198.2 |
| 5,486,410 A | 1/1996 | Groeger | 428/283 |
| 5,785,925 A | 7/1998 | U'Ren | 422/72 |
| 5,801,055 A | 9/1998 | Henderson | 435/297.5 |
| 5,906,796 A | 5/1999 | Blevins | 422/102 |
| 5,979,669 A | 11/1999 | Kitajima et al. | 210/455 |
| 6,043,027 A | 3/2000 | Selick et al. | 435/4 |
| 6,190,559 B1 * | 2/2001 | Valaskovic | 210/656 |
| 6,254,780 B1 * | 7/2001 | Bouvier et al. | 210/635 |
| 6,254,789 B1 | 7/2001 | Marion | 210/765 |
| 6,387,273 B1 | 5/2002 | Abedi | 210/656 |
| 6,395,183 B1 * | 5/2002 | Valaskovic et al. | 210/656 |
| 6,440,301 B1 * | 8/2002 | Dobos | 210/198.2 |
| 6,458,273 B1 * | 10/2002 | Krakover et al. | 210/198.2 |

OTHER PUBLICATIONS

Wheat, "Mass-directed AutoPurification", 48th ASMS Conference on Mass Spectrometry and Allied Topics, (Jun. 11, 2000), pp. 1-31.

* cited by examiner

DEVICE FOR SOLID PHASE EXTRACTION AND METHOD FOR PURIFYING SAMPLES PRIOR TO ANALYSIS

CROSS REFERENCE TO RELATED APPLICATIONS

This application is a divisional of application Ser. No. 10/100,762 filed Mar. 19, 2002, now U.S. Pat. No. 6,723,236. The contents of the aforementioned application are hereby expressly incorporated herein by reference in their entirety.

BACKGROUND OF THE INVENTION

Solid phase extraction (SPE) is a chromatographic technique for preparing samples prior to performing quantitative chemical analysis, for example, via high performance liquid chromatography (HPLC), or gas chromatography (GC). The goal of SPE is to isolate target analytes from a complex sample matrix containing unwanted interferences, which would have a negative effect on the ability to perform quantitative analysis. The isolated target analytes are recovered in a solution that is compatible with quantitative analysis. This final solution containing the target compound can be directly used for analysis or evaporated and reconstituted in another solution of a lesser volume for the purpose of further concentrating the target compound, making it more amenable to detection and measurement.

Depending on the type of analysis to be performed, and detection method used, SPE may be tailored to remove specific interferences. Analysis of biological samples such as plasma and urine using high performance liquid chromatography (HPLC) generally requires SPE prior to analysis both to remove insoluble matter and soluble interferences, and also to pre-concentrate target compounds for enhanced detection sensitivity. Many sample matrices encountered in bio-separations contain buffers, salts, or surfactants, which can be particularly troublesome when mass spectrometer based detection is used. SPE can also be used to perform a simple fractionation of a sample based on differences in the chemical structure of the component parts, thereby reducing the complexity of the sample to be analyzed.

Devices designed for SPE typically include a chromatographic sorbent which allows the user to preferentially retain sample components. Once a sample is loaded onto the sorbent, a series of tailored washing and elution fluids are passed through the device to separate interferences from target sample components, and then to collect the target sample components for further analysis. SPE devices usually include a sample holding reservoir, a means for containing the sorbent, and a fluid conduit, or spout for directing the fluids exiting the device into suitable collection containers. The SPE device may be in a single well format, which is convenient and cost effective for preparing a small number of samples, or a multi-well format, which is well suited for preparing large numbers of samples in parallel. Multi-well formats are commonly used with robotic fluid dispensing systems. Typical multi-well formats include 48-, 96-, and 384-well standard plate formats. Fluids are usually forced through the SPE device and into the collection containers, either by drawing a vacuum across the device with a specially designed vacuum manifold, or by using centrifugal or gravitational force. Centrifugal force is generated by placing the SPE device, together with a suitable collection tray, into a centrifuge specifically designed for the intended purpose.

Various means have been used to contain chromatographic sorbents within SPE devices. A common method, described in U.S. Pat. No. 4,211,658, utilizes two porous filters, with chromatographic sorbent contained between the filters. In this design, the SPE device is essentially a small chromatographic column containing a packed bed of sorbent. A variation of this design is described in U.S. Pat. No. 5,395,521, where the porous filter elements are spherical in shape. In U.S. Pat. No. 4,810,381, the chromatographic sorbent is immobilized within a thin porous membrane structure. In EP Application No. 1110610A1 a method is described for securing these filters within the SPE device by means of a sealing ring pressed around the periphery of the membrane disc. In U.S. Pat. No. 5,486,410 a fibrous structure containing immobilized functional materials is described. In U.S. Pat. No. 5,906,796 an extraction plate is described where glass fiber discs containing chromatographic sorbent are press fit into each well of the SPE device.

A number of chromatographic sorbents can be used depending on the nature of the sample matrix and target compounds. A common example is to use porous silica that has been surface derivatized with octydecyl ($C_{18}$) or octyl ($C_8$) functional groups. Porous particles that are based on organic polymers are also widely used. One such type, which is particularly well suited for SPE due to its high loading capacity and unique retention properties, is described in U.S. Pat. No. 6,254,780.

Typical SPE methods contain a sequence of steps, each with a specific purpose. The first step, referred to as the "conditioning" step, prepares the device for receiving the sample. For reversed-phase SPE, the conditioning step involves first flushing the SPE device with an organic solvent such as methanol or acetonitrile, which acts to wet the surfaces of both the device and the sorbent, and also rinses any residual contaminants from the device. This initial rinse is generally followed with a highly aqueous solvent rinse, often containing pH buffers or other modifiers, which will prepare the chromatographic sorbent to preferentially retain the target sample components. Once conditioned, the SPE device is ready to receive the sample.

The second step, referred to as the "loading" step, involves passing the sample through the device. During loading, the sample components, along with many interferences are adsorbed onto the chromatographic sorbent. Once loading is complete, a "washing" step is used to rinse away interfering sample components, while allowing the target compounds to remain retained on the sorbent. The washing step is then followed by an "elution" step, which typically uses a fluid containing a high percentage of an organic solvent, such as methanol or acetonitrile. The elution solvent is chosen to effectively release the target compounds from the chromatographic sorbent, and into a suitable sample container.

In many cases, elution with high concentrations of organic solvent requires that further steps be taken before analysis. In the case of chromatographic analysis (HPLC), it is highly desirable for samples to be dissolved in an aqueous-organic mixture rather than a pure organic solvent, such as methanol or acetonitrile. For this reason, SPE samples eluted in pure acetonitrile or methanol are usually evaporated to dryness ("drydown"), and then reconstituted in a more aqueous mixture ("reconstitution") before being injected into an HPLC system. These additional steps not only take time and effort, but can also lead to loss of valuable sample, either through target analyte loss onto collection container surfaces during drydown, or due to target analyte evaporative losses or difficulties encountered when trying to re-dissolve the dried sample in the higher percent aqueous fluid.

It can be seen then, that it is advantageous for an SPE device to have a high capacity for retaining target compounds of a wide range of chromatographic polarities, to be capable of maintaining target compound retention as sample interferences are washed to waste, and then to provide the capability to elute target compounds in as small an elution volume as possible, thereby maximizing the degree of target compound concentration obtained during SPE.

The ability to elute in very small volumes of solvent has the added benefit of minimizing the amount of time required to evaporate and reconstitute the sample before proceeding with analysis if further concentration or solvent exchange is required. If elution volume can be kept very low, then drydown and reconstitution can be entirely eliminated.

Traditional SPE device designs have attempted to address these issues, each with a limited measure of success. Packed bed devices utilize packed beds of sorbent particles contained between porous filter discs that are press fit into the SPE device. The capture efficiency of the resulting packed beds is typically quite good, especially if the sorbent properties are carefully chosen. One drawback with conventional packed bed devices is that the void volume contained within the porous filters and packed bed requires that relatively large elution volumes be used to completely elute the target compounds. Typical elution volumes required to fully elute target compounds from a packed bed type SPE device fall in the range of 200–5000 µL, depending on the size of the sorbent bed.

Membrane based designs attempt to address this issue by embedding sorbent particles within a fluorocarbon based membrane, which are then placed into the SPE device. A small mass of sorbent particles is embedded into a thin membrane structure with a wide cross sectional area. Since the membrane does not require retaining filters, the volume associated with the two porous filters is eliminated. This approach reduces the total volume contained within the device, and therefore the volume of solvent required for elution. A typical elution volume required to fully elute target compounds from a particle in membrane SPE device fall in the range of 75–500 µL. Designs of this type have drawbacks in other areas however. The sorbent particles are less densely packed within the membrane structure than within a packed bed, leading to poorer capture efficiency, and a greater chance that target compounds will break through the device without being well retained. In addition, the flow properties of the membrane can be highly variable, due to the poor wetting characteristics of the fluorocarbon based membrane when using highly aqueous fluids.

In U.S. Pat. No. 5,906,796 a design is described in which glass fiber based extraction discs containing chromatographic particles are press fit into each well of the SPE device. Like the membrane designs, this approach immobilizes the sorbent particles in a thin sheet, thereby minimizing device void volume and required elution volumes. Typical volumes required to fully elute target compounds from an SPE device such as this fall in the range of 75–500 µL, which is comparable to particle-in-membrane devices. The sorbent particles are even less densely packed than with membranes however, so sample breakthrough tends to be higher than with either membrane or packed bed devices, and sorbent particles can often break free from the fibrous matrix and contaminate the collected sample solution. One advantage over membrane devices is that flow problems due to wetting issues are generally less common due to the more open structure of the glass fiber disc. One disadvantage of this particle embedded glass fiber disk is that it contains silanol groups that interact with basic compounds. This requires the use of more complex elution solvents, for example, the addition of 2% base or acid to the elution solvent, to maintain the 75–500 µL elution volumes.

It can be seen then, that the lower elution volume capability achieved with both the membrane and glass fiber approaches is at the expense of target compound breakthrough during loading and/or poor recovery for non-polar compounds. Although the volume of fluid needed to effectively elute samples from the membrane and glass fiber formats is reduced to approximately one half of the volume required with conventional packed bed based devices, drydown and reconstitution steps are still required before samples can be further analyzed by HPLC.

SUMMARY OF THE INVENTION

The present invention relates to an improved SPE device which has been specifically designed to contain a small packed bed of chromatographic sorbent such that the bed provides for highly efficient retention of target compounds, while the volume contained within the sorbent bed is sufficiently small as to allow for efficient elution of sample compounds in a minimal elution volume. Specifically, the solid phase extraction device of the present invention comprises a reservoir with an opening; a well comprising an internally tapered wall, the well having a wider interior diameter at an end closest to the opening than at an exit spout; a first filter within the well; a bed of sorbent particles within the well below the first filter; and a second filter having a smaller diameter than the first filter within the well below the bed of sorbent particles and above the exit spout.

The present invention provides a large bed height to top bed diameter ratio using a significantly smaller sorbent mass than is present in current state of the art devices. The large bed height to bed diameter ratio enhances the retention of target compounds and helps to prevent breakthrough of these compounds during the load and wash steps. In SPE the first filter and the top of the sorbent bed acts like a depth filter in removing insoluble sample components. The larger diameter for the upper portion of the bed and larger diameter first filter allows the device to draw through larger sample volumes than could be drawn through a device having an upper bed diameter the same as the lower bed diameter before obstructions will occur. The smaller second filter increases the bed height to bed diameter ratio for a given mass of sorbent while reducing the hold up volume of the device which minimizes required elution volumes.

Moreover, the present invention provides for conically shaped packed beds contained between spherical filters which enhance the performance of solid phase extraction devices by allowing target compounds to be both efficiently retained and eluted. The larger first spherical filter provides a surface area that is approximately two times the area of an equivalently sized cylindrical filter. For example, surface area of the top half of a sphere ($\pi/2 \times d^2$) of a diameter of 0.1" is equal to the surface area of the top of a disk of diameter 0.14" ($\pi/4 \times d^2$). The smaller second filter helps to minimize the amount of sorbent needed to create a bed length that will be free of adverse imperfections.

The present invention enables the retention of target compounds with a wide range of chromatographic polarity with elution in volumes that are much reduced from the current state of the art for solid phase extraction. This reduction in elution volume provides a solution containing the target compounds that can be diluted with an aqueous solution while still maintaining the high sample concentrations required for analysis.

According to another aspect, the present invention provides an enhanced method of performing solid phase extraction, where the volume of elution solvent is sufficiently small so as to eliminate the need for an evaporation step. The method involves elution of the target compounds in a minimal volume of organic solvent, typically 10–40 µL, which is then diluted with a highly aqueous fluid to form an aqueous organic sample mixture. This mixture is suitable for direct analysis by HPLC, thereby eliminating the time, expense, and potential sample losses associated with evaporation and reconstitution steps, while still maintaining a high degree of target compound(s) concentration.

Specifically, the inventive method comprises the steps of providing the above-mentioned SPE device, and isolating target substances from interfering components in a sample medium, wherein the target substances are substantially eluted in less than 50 µL volume.

In one embodiment of the present invention, the isolating step of the present invention preferably includes conditioning the SPE device with an organic solvent; equilibrating the SPE device with an aqueous solution; adding a prepared sample containing the target substances and interfering components to the SPE device; washing the SPE device with an aqueous solution to remove interfering components; and eluting the adsorbed target substances.

In a preferred embodiment of this enhanced method of the present invention, the aqueous diluent is added directly through the SPE device, while still on the processing station used to perform the SPE fluid transfers. In this way, residual elution solvent is swept through the device into the collection container, where it is diluted by the aqueous fluid and mixed by the gentle air stream that is drawn through the well at the end of the transfer. This approach has the advantage of eliminating the need for a separate pipetting operation to perform the dilution step.

DETAILED DESCRIPTION OF THE INVENTION

Figure 1:
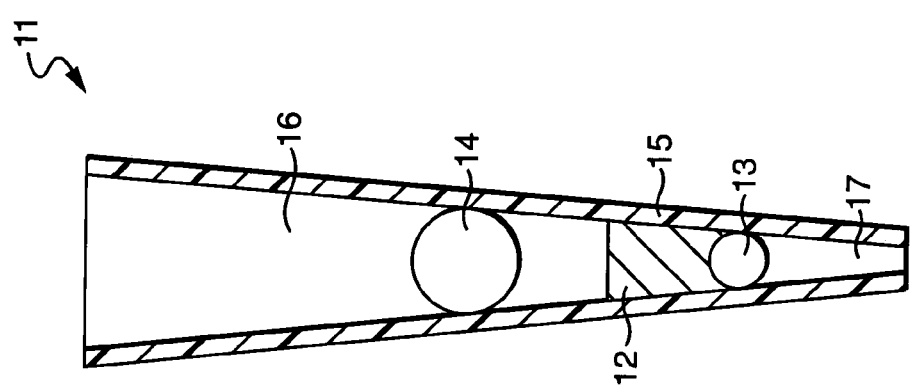
FIG. 1 is an illustration of a single well embodiment of the present invention, where the internal well geometry is a simple tapered shape, containing two spherical filter elements of different sizes, a bed of sorbent particles contained between the filters, an exit spout downstream from the smaller filter, and a fluid reservoir upstream from the larger porous filter.

FIG. 1 shows an SPE device of packed bed design where the device has been optimized for high capture efficiency, while requiring minimal elution volume. The device (11) contains a small bed of sorbent particles (12), contained between two porous filter elements of different sizes (13 & 14) within a tapered internal well geometry (15), such that the porous filter (13) positioned downstream from the sorbent bed (12) is smaller than the porous filter (14) positioned upstream from the sorbent bed. The device also includes a reservoir section (16) located upstream from the larger porous filter (14) and an exit spout (17) located downstream from the smaller porous filter (13). The spout directs fluids exiting the device into a suitable collection container (not shown).

Porous filters (13 & 14) may be of any material suitable for retaining the sorbent particles. In a preferred embodiment, porous filters (13 & 14) are made from sintered polyethylene material. FIG. 1 represents a single well version of the device, although it will be obvious to one skilled in the art, that the device may also be configured as part of a multi-well SPE device.

In this preferred embodiment of the SPE device of the present invention, the porous filters that contain the sorbent particles are spherical in shape, and the sorbent bed is configured in a tapered geometry, with the downstream porous spherical filter being smaller than the upstream porous spherical filter.

The sorbent particles employed in the device include any particulate matter that is capable of having at least one substance, either target or interfering, adhered thereto. Illustrative examples of sorbent particles that may be employed in the present invention include, but are not limited to: ion exchange sorbents, reversed phase sorbents, and normal phase sorbents. More particularly, the sorbent particles may be an inorganic material such as $SiO_2$ or an organic polymeric material such as poly(divinylbenzene). In some embodiments of the present invention, the sorbent particles may be treated with an organic functional group such as a $C_2$–$C_{22}$, preferably $C_8$–$C_{18}$ functional group. One skilled in the art will find it obvious that the size, shape, surface area, and pore volume of the sorbent particles, may all be modified to suit specific applications without departing from the scope of the invention.

The tapered internal device geometry acts to provide an upstream first porous filter having a large filtration area for capturing foreign sample particulates prior to them reaching the sorbent bed, and a smaller downstream filter, while allowing minimal internal void volume between the sorbent bed and the first filter. The effective filtration area of the spherical filter is based on the surface of the exposed hemispherical section of the filter, which is larger than the area of a flat disc filter of equal diameter by a factor of 2.

The spherical filters are easy to handle during assembly and require no special insertion tooling. Moreover, the spherical filters self-align when placed into a tapered well cavity, and seal against the cavity wall easily without the need for close dimensional tolerances between the spherical filters and the internal surface of the well. The tapered well design also allows for a range of sorbent masses within the same SPE device, thereby providing flexibility to tailor the device for different applications. This is accomplished by simply changing the diameter of the spherical porous filters, thereby positioning the filters and packed sorbent bed either higher or lower within the tapered device without having to alter the well cavity.

The tapered well geometry differs from conventional cylindrical designs, since it results in a sorbent bed shape that has considerably less tendency to form undesirable flow channels, thereby preventing sample components bypassing the bed without adequately contacting the sorbent particles. Fluids passing through the sorbent bed during the conditioning and loading steps act to consolidate the tapered packed bed, resulting in a consistently formed bed structure. This results in efficient contact between the sample and the sorbent bed, less chance for sample breakthrough during loading, and efficient use of wash and elution fluids.

Figure 2:
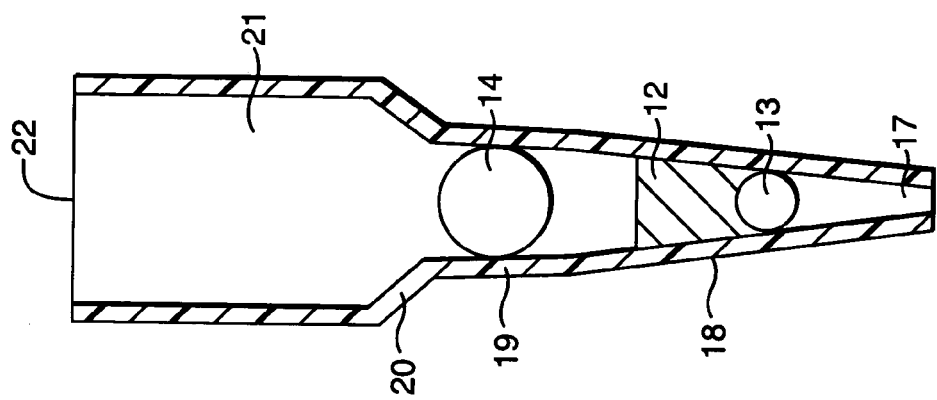
FIG. 2 is an illustration of a single well embodiment of the present invention where the internal tapered well geometry is segmented, providing an exit spout downstream from the smaller porous filter, a lower tapered section containing both the smaller porous filter and a bed of sorbent particles, an upper tapered section which contains the larger porous filter upstream from the sorbent bed, and a transition section leading to an upper fluid reservoir.

FIG. 2 is an illustration of a single well embodiment of the present invention where the internal tapered well geometry is segmented, providing an exit spout (17) downstream from the smaller second porous filter (13), a lower tapered section (18) containing both the smaller porous filter (13) and a bed of sorbent particles (12), an upper tapered section (19) which contains the larger first porous filter (14) upstream from the sorbent bed (12), and a transition section (20) leading to an upper fluid reservoir (21) having a larger diameter opening (22). Segmentation of the internal taper in this way allows for SPE devices which have larger capacity reservoirs while maintaining the advantages of the present invention in a relatively short overall well height.

Figure 3:
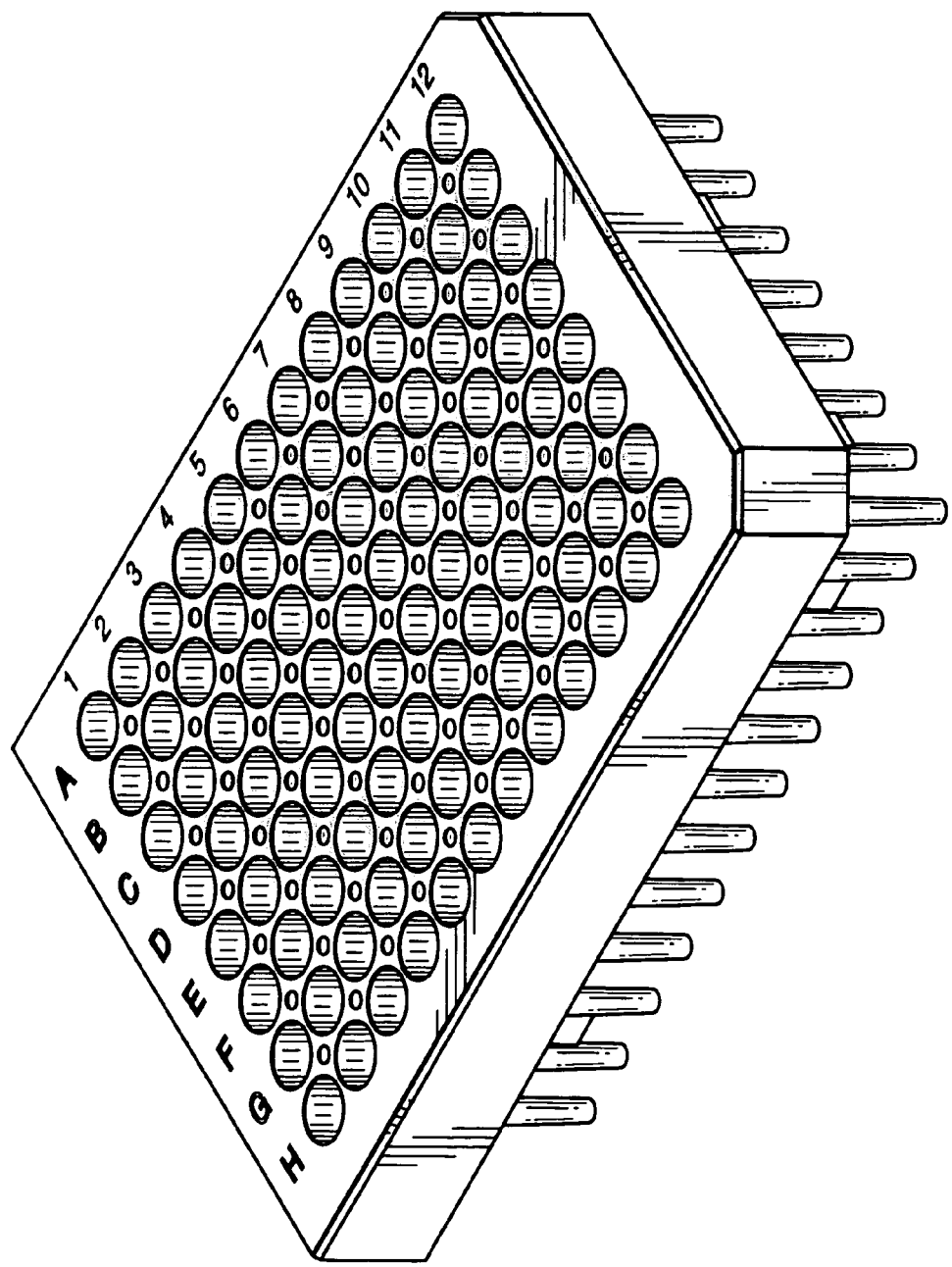
FIG. 3 is an illustration of a multi-well SPE device where each well of the device contains the single well device geometry of FIG. 2.

FIG. 3 is an illustration of a multi-well version of an SPE device incorporating the single well design of FIG. 2. Common multi-well formats include plate designs based on the common 48, 96, and 384 standard well formats.

Figure 6:
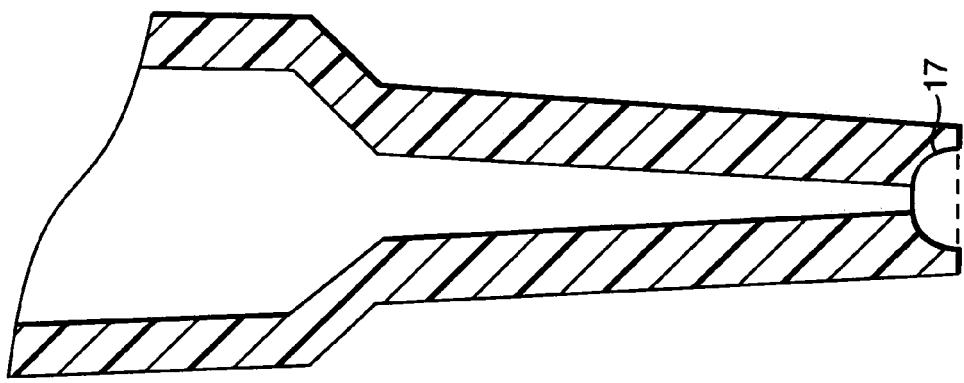
FIG. 6 is an illustration of a semi-circular exit spout of the device.
Figure 5:
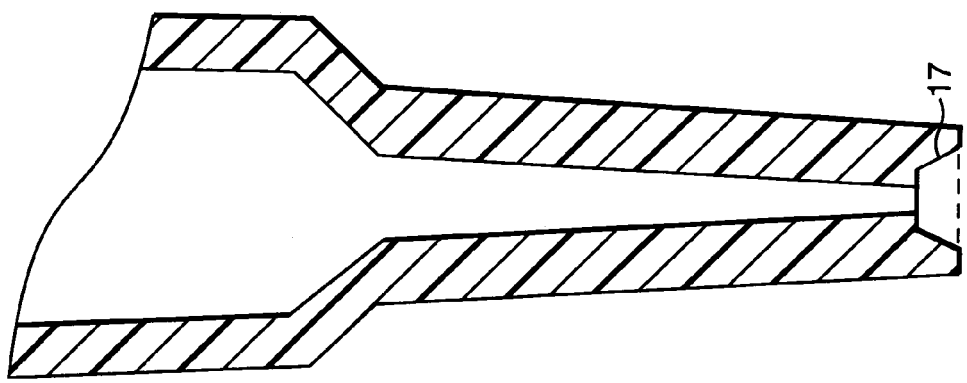
FIG. 5 is an illustration of a trapezoidal exit spout.

The exit spout directs fluids into any suitable container. In the preferred embodiment, shown in FIG. 5, the exit spout 17 geometry is substantially trapezoidal. This geometry is used to prevent the exiting fluids from creeping up the exterior wall of the device and provides effective beading and dropping of the exiting fluids. A semi-circular shape may also be used for the exit spout 17 as shown in FIG. 6.

The present invention can be used to purify samples prior to analysis, i.e., to isolate a desired target substance from an interfering substance in a sample medium, using a smaller elution volume than heretofore possible with prior art SPE devices. Specifically, and in a preferred embodiment, the method of the present invention comprises first conditioning the SPE device with any organic solvent that is capable of wetting the surfaces of the device and sorbent particles. Illustrative examples of organic solvents that can be used in the conditioning step include, but are not limited to: polar or non-polar organic solvents such as methanol and acetonitrile. The amount of organic solvent used to condition the SPE device may vary and is not critical to the present invention so long as the organic solvent is used in an amount that wets the SPE device. Note that the solvent used in this step of the inventive method also serves to remove contaminants from the SPE device.

After the conditioning step, an aqueous solution is used to equilibrate the conditioned SPE device. The amount of aqueous solution used to equilibrate the SPE device may vary and is not critical to the present invention.

A prepared sample containing at least one target substance as well as interfering components is then added to the SPE device using conventional means that are well known to those skilled in the art. The inventive method is not limited to a specific prepared sample or target substance. For example, the prepared sample may be blood plasma, serum, urine, and other like samples that are capable of being purified by solid phase extraction. Insofar as the target substance is concerned, the inventive SPE method works well on polar compounds, non-polar compounds, acidic compounds, neutral compounds, basic compounds and any mixtures thereof.

Next, an aqueous solution is employed to remove the interfering substance from the SPE device and thereafter the target substance, which is adsorbed onto the sorbent particles, is eluted from the SPE device using an organic eluant that is capable of removing the adsorbed target substances from the SPE device.

The following examples are given to illustrate the scope of the present invention. Because these examples are given for illustrative purposes only, the present invention is not limited to the following examples.

EXAMPLES

Example 1

A spherical porous polyethylene filter having a diameter of 0.075" is press sealed into a molded well cavity having a 5° included angle taper as shown in FIG. 2. A packed bed is formed within the 5° tapered well using 2 milligrams of Waters' Oasis® HLB, 30 micron sorbent particles. A spherical porous polyethylene filter having a diameter of 0.100" is press sealed into the upper section of the well which contains a 1° included angle. The upper porous filter acts to both contain the sorbent particles within the well, and to act as a sample pre-filter.

Example 2

A spherical porous polyethylene filter having a diameter of 0.058" is press sealed into a well having a 5° included angle taper as in EXAMPLE 1. A packed bed is formed within the 5° tapered well using 1 milligram of Waters' Oasis® HLB brand, 30 micron sorbent particles. A spherical porous polyethylene filter having a diameter of 0.100" is press sealed into the upper section of the well to both contain the sorbent particles within the well, and to act as a sample pre-filter. The resulting device contains one half the amount of sorbent as in EXAMPLE 1, but due to the smaller lower filter size, the bed is positioned lower in the tapered well, with a bed shape that is well suited for effective performance.

Example 3

The SPE device of EXAMPLE 1 is placed on a vacuum manifold station with a collection vial positioned below the exit spout to collect fluids exiting the device. A vacuum of 10" Hg is applied to draw fluids through the device. The device is first conditioned by passing 100 μL methanol through the device, followed by 100 μL water. A spiked plasma sample is prepared by spiking 250 μL porcine plasma with 1.9 μg of amitriptyline, followed by dilution with 250 μL of 2% phosphoric acid in water. The diluted spiked plasma sample is then drawn through the device. After addition of the diluted, spiked plasma sample, the sorbent bed is washed using 100 μL water. An elution step is then performed by passing 25 μL acetonitrile/methanol (80/20 by volume) through the sorbent bed, and collecting into a clean collection vial. The resulting sample mixture contains the target compound, free from plasma interferences, concentrated ten fold. The sample solution may be analyzed directly, or further evaporated and reconstituted in a solvent mixture suitable for the intended analysis.

Example 4

The SPE device of EXAMPLE 1 is used in identical manner as described in Example 3, except that after eluting with 25 μL acetonitrile/methanol (80/20 by volume), an additional 25 μL water is drawn through the sorbent bed and into the same vial which contains the previously eluted sample compound. The resulting sample mixture contains the target compound, free from plasma interferences, concentrated five fold in a 50% aqueous/organic solution, which is well suited for direct analysis using HPLC.

Example 5

The model target compounds acetaminophen, N-acetyl-procainamide, betamethasone, caffeine, naproxen, amitriptyline, and propranolol were obtained from Sigma Aldrich. The model target compound practolol was purchased from Tocris. The Octadecyl ($C_{18}$) SD-C18 3M Empore™ High Performance Extraction Disk Plate (PN 6015) was purchased from Fisher Scientific. The Universal Resin (UR) 3M Empore™ High Performance Extraction Disk Plate (PN 6345) was purchased from VWR. The Ansys® Technologies, INC. Spec·C18 96-Well Plate (PN 596-03) was purchased from Ansys Technologies, INC. The 5 mg Oasis® HLB Extraction Plate was purchased from Waters (PN 186000309). A 2 mg amount of Oasis® HLB (Waters Corporation) was packed into a device similar to that shown in FIG. 1 with the sorbent contained between a lower polyethylene spherical frit of a diameter of 0.08" at the outlet and an upper polyethylene spherical frit of a diameter of 0.1" at the inlet. Organic solvents were obtained from VWR (J. T. Baker HPLC grade).

Stock 1 mg/mL solutions of each of the following model target compounds were made in 20/80 methanol/water (v/v): acetaminophen, practolol, N-acetyl procainamide, caffeine, propranolol, and amitriptyline. Stock 1 mg/mL solutions of each of the following model target compounds were made in 80/20 methanol/water (v/v): naproxen, betamethasone, and ibuprofen. The internal standard solution was prepared by adding equal parts of the ibuprofen stock solution to water (1:1). Appropriate amounts of the stock solutions were added to a pH 7 isotonic saline solution to achieve the following concentration of model target compounds:

| Compound | Concentration In Saline Test Mix |
|---|---|
| practolol | 5 μg/mL |
| n-acetyl procainamide | 7.5 μg/mL |
| acetaminophen | 5 μg/mL |
| caffeine | 7.5 μg/mL |
| naproxen | 5 μg/mL |
| Amitriptyline | 7.5 μg/mL |
| betamethasone | 2.5 μg/mL |
| propranolol | 40 μg/mL |
| Phenyl acetic acid | 150 μg/mL |

The isotonic saline solution was prepared by adding 0.4 g KCl, 16.00 g NaCl, 0.4 g $KH_2PO_4$, and 2.3 g $Na_2HPO_4$ to 3 liters of water. The mixture was allowed to dissolve completely before adjusting to pH 7 with concentrated $H_3PO_4$.

All solid phase extraction devices were conditioned with 100 μL of methanol, followed by 100 μL of water. Care was taken not to allow the sorbent to dry out between the methanol and water rinse steps. 100 μL of the saline solution containing the target model compounds was drawn through the device typically using <4"Hg vacuum. 100 μL of water was drawn through the device to wash the sorbent. 25 μL or 75 μL of an 80/20 acetonitrile/methanol solution was drawn through the device to elute the model target compounds. 50 μL of a 0.5 mg/mL ibuprofen internal standard solution and an additional 25 μL of saline was added to each sample prior to analysis.

| Samples were analyzed by HPLC using the following gradient of 0.01% formic acid (D) to acetonitrile (C): | | | | | | |
|---|---|---|---|---|---|---|
| Time | Flow | % A | % B | % C | % D | Curve |
|  | 2.00 | 0.0 | 0.0 | 0.0 | 100.0 |  |
| 7.33 | 2.00 | 0.0 | 0.0 | 65.0 | 35.0 | 6 |
| 8.60 | 3.00 | 0.0 | 0.0 | 100.0 | 0.0 | 1 |
| 8.84 | 4.00 | 0.0 | 0.0 | 100.0 | 0.0 | 1 |
| 9.00 | 2.00 | 0.0 | 0.0 | 0.0 | 100.0 | 1 |
| 9.50 | 3.00 | 0.0 | 0.0 | 0.0 | 100.0 | 1 |
| 15.00 | 2.00 | 0.0 | 0.0 | 0.0 | 100.0 | 6 |
| 35.00 | 2.00 | 0.0 | 0.0 | 100.0 | 0.0 | 11 |
| 45.00 | 0.00 | 0.0 | 0.0 | 100.0 | 0.0 | 11 |

The column temperature was maintained at 30° C. using a Spark Holland Mistral heater box. The HPLC system consisted of a Waters 600E Solvent Delivery System, a Waters 717plus Autosampler, a Waters in-line vacuum degasser, and a Waters 2487 Tunable UV detector set to 254 nm (sampling rate=2 points/sec). Millennium$^{32}$ Chromatography Manager v3.20 was used for data acquisition and processing, and equipment control.

Separations were performed using a 3.5 μm Symmetry Shield RP8 4.6×75 mm (Waters part number Wat094263) column with a 5 μm Symmetry Shield RP8 Sentry 3.9×20 mm guard column (Waters Part Number Wat200675). The injection volume was 10 μL for all standards, controls, and samples. The total run time was 15 min.

The hold-up volume was determined for each of the devices tested. It was determined by adding 50 μL or 75 μL, depending on estimates of the device's hold-up volume, of 50/50 isopropanol/water to 4 wells each. The solution was allowed to soak into the beds for 30 sec. A vacuum of first 4"Hg for 45 sec then 7"Hg for 45 sec was used to draw the solution through the devices and into total recovery vials (Waters PN186000837). The volume of solution in the vials was measured using an auto-pipette. The hold-up volume was determined by subtracting the collected volume from the added volume.

The recovery results in Table 1 show the performance difference between what is commercially available on the market today and this new tip design. The data shows that recoveries in 25 μL volumes ranged from 84% to 97% on the new tip device compared to 51%–86% on the best performing commercially available device today, which also contains the same sorbent. This direct comparison illustrates how the new device format improves recoveries. Devices containing particles embedded in glass fibers or Teflon had recoveries that were substantially lower (0 to 64%).

The target compounds are listed in Table 1 from the most polar at the top of the list to the least polar. On the Oasis® HLB 5 mg 96-well plate, the recovery results sharply decrease as the polarity of the compounds decreases. The new tip device is able to give high recoveries for compounds having a wide range of chromatographic polarities.

TABLE 1

% Recoveries (n = 4) in 25 μL Elution Volumes with 80/20 Acetonitrile/Methanol

| | Inventive Device† Oasis® HLB 2 mg packed bed | Oasis® HLB 5 mg Plate packed bed | Ansys® Spec Plus C18 Plate glass fiber disk | 3M Empore™ Universal Resin teflon disk |
|---|---|---|---|---|
| | Elution Volume | | | |
| | 25 μL | 25 μL | 25 μL | 25 μL |
| N-acetyl procainamide | 95.6 | 85.8 | 0 | 6.9 |
| practolol | 92.8 | 83.6 | 0 | 7.7 |
| acetaminophen | 93.1 | 77.5 | 50.4* | 9.1 |
| caffeine | 97.0 | 82.3 | 41.3 | 9.8 |
| propranolol | 89.3 | 70.2 | 0 | 1.8 |
| amitriptyline | 83.6 | 59.1 | 0 | 0 |
| betamethasone | 91.5 | 59.9 | 24.3 | 0.7 |
| naproxen | 84.1 | 50.8 | 64.4 | 5.3 |
| Max Recovery | 97 | 86 | 64 | 10 |
| Min Recovery | 84 | 51 | 0 | 0 |

†Replicates of 3.
*Breakthrough in the load and wash was 27%.

All others show <5% breakthrough.

The relative standard deviations (% RSDs) for the recoveries are shown in Table 2. They range from 0.9%–4% on the new tip design versus 4.6%–10.5% on the best performing current state of the art device. Results with equivalent recoveries and reproducibilities to those obtained on the new tip design were not obtained on the existing 96-well plates with less than 75 μL elutions. For all quantitative analytical work good reproducibility is essential and high recovery is desirable. For high sensitivity quantitative analytical work both are essential: good reproducibility and high recovery.

TABLE 2

% RSDs (n = 4) for Recoveries in 25 μL Elution Volumes with 80/20 Acetonitrile/Methanol

| | Inventive Device† Oasis® HLB 2 mg packed bed | Oasis® HLB 5 mg Plate packed bed | Ansys® Spec Plus C18 Plate glass fiber disk | 3M Empore™ Universal Resin teflon disk |
|---|---|---|---|---|
| | Elution Volume | | | |
| | 25 μL | 25 μL | 25 μL | 25 μL |
| N-acetyl procainamide | 0.9 | 5.0 | | 72.9 |
| Practolol | 1.2 | 6.1 | | 69.1 |
| Acetaminophen | 1.6 | 6.4 | 10.0 | 59.2 |
| Caffeine | 1.7 | 4.6 | 8.6 | 58.0 |
| Propranolol | 1.6 | 6.7 | | 71.3 |
| Amitriptyline | 4.0 | 7.6 | | — |
| Betamethasone | 2.5 | 8.6 | 13.5 | 200.0 |
| Naproxen | 2.5 | 10.5 | 3.2 | 73.0 |
| Max RSD | 4.0 | 10.5 | 13.5 | 200.0 |
| Min RSD | 0.9 | 4.6 | 3.2 | 58.0 |

†Replicates of 3.

Table 3 shows the recovery results obtained using a 75 μL elution volume on commercially available 96 well SPE plates that have been specifically designed to minimize elution volume. The shortcoming of the Oasis HLB 5 mg plate is that the recoveries vary with the polarity of the compounds due to insufficient elution volume. The shortcomings of the Ansys® device are two fold. First recoveries of the basic compounds are extremely poor due to secondary interactions with the sorbent and glass fiber. The addition of about 2% acetic acid or 2% ammonium hydroxide to the elution solvent would improve recoveries. The manufacturer of this device recommends using 500 μL or less to elute compounds from this device.

Neutral model compounds like caffeine, a polar compound, and betamethasone, a non-polar compound, do not suffer from this problem. The 78.9% recovery for caffeine, and 67.6% recovery for betamethasone show that 75 μL is not an adequate elution volume to recover a broad polarity range of compounds from the Ansys plate.

The 3M Empore™ devices also show recovery problems for the bases. In addition, the 51% and 56% recoveries for betamethasone show that 75 μL elution volumes are not adequate to elute a broad polarity range of compounds from these devices. All four of these devices also suffer from breakthrough of acetaminophen, a polar neutral compound.

TABLE 3

% Recovery (n = 4) in 75 μL Elution Volumes with 80/20 Acetonitrile/Methanol for Different 96-well Formats

| | Oasis® HLB plate 5 mg packed bed | Ansys® Spec Plus C18 plate glass fiber disk | 3M Empore™ Universal Resin plate Teflon disk | 3M Empore™ C18-SD plate Teflon disk |
|---|---|---|---|---|
| | Elution Volume | | | |
| | 75 μL | 75 μL | 75 μL | 75 μL |
| N-acetyl procainamide | 85.2 | 7.0 | 57.4 | 73.3 |
| Practolol | 81.7 | 19.8 | 56.0 | 82.3** |
| acetaminophen | 86.3** | 68.2* | 71.5** | 76.6* |
| Caffeine | 93.1 | 78.9 | 75.1 | 92.9 |
| Propranolol | 83.8 | 1.8 | 33.5 | 41.5 |
| Amitriptyline | 85.3 | 0.6 | 20.1 | 6.1 |
| betamethasone | 87.8 | 67.6 | 51.1 | 55.6 |
| Naproxen | 79.9 | 85.0 | 62.8 | 70.8 |
| Max Recovery | 93.1 | 85.0 | 75.1 | 92.9 |
| Min Recovery | 79.9 | 0.6 | 20.1 | 6.1 |

*Breakthrough in the load and wash was 19–20%.
**Breakthrough in the load and wash was 5–8%.

All others show <5% breakthrough.

TABLE 4

% RSDs for Recoveries (n = 4) in 75 μL Elution Volumes with 80/20 Acetonitrile/Methanol for Different 96-well Formats

| | Oasis® HLB plate 5 mg | Ansys® Spec Plus C18 plate glass fiber disk | 3M Empore™ Universal Resin plate teflon disk | 3M Empore™ C18-SD plate teflon disk |
|---|---|---|---|---|
| | Elution Volume | | | |
| | 75 μL | 75 μL | 75 μL | 75 μL |
| N-acetyl procainamide | 9.7 | 21.3 | 9.1 | 5.5 |
| Practolol | 10.6 | 24.0 | 8.8 | 3.6 |
| acetaminophen | 5.9 | 4.5 | 8.5 | 10.8 |
| Caffeine | 3.9 | 9.5 | 8.6 | 3.1 |
| Propranolol | 6.9 | 138.8 | 4.3 | 19.5 |
| Amitriptyline | 3.8 | 200.0 | 13.8 | 47.5 |
| betamethasone | 1.3 | 16.7 | 5.5 | 35.0 |
| Naproxen | 3.0 | 3.1 | 7.7 | 19.1 |

TABLE 4-continued

% RSDs for Recoveries (n = 4) in 75 μL Elution Volumes
with 80/20 Acetonitrile/Methanol for Different 96-well Formats

|  | Oasis® HLB plate 5 mg | Ansys® Spec Plus C18 plate glass fiber disk | 3M Empore™ Universal Resin plate teflon disk | 3M Empore™ C18-SD plate teflon disk |
|---|---|---|---|---|
|  | Elution Volume | | | |
|  | 75 μL | 75 μL | 75 μL | 75 μL |
| Max RSD | 10.6 | 200.0 | 13.8 | 47.5 |
| Min RSD | 1.3 | 3.1 | 4.3 | 3.1 |

Figure 4:
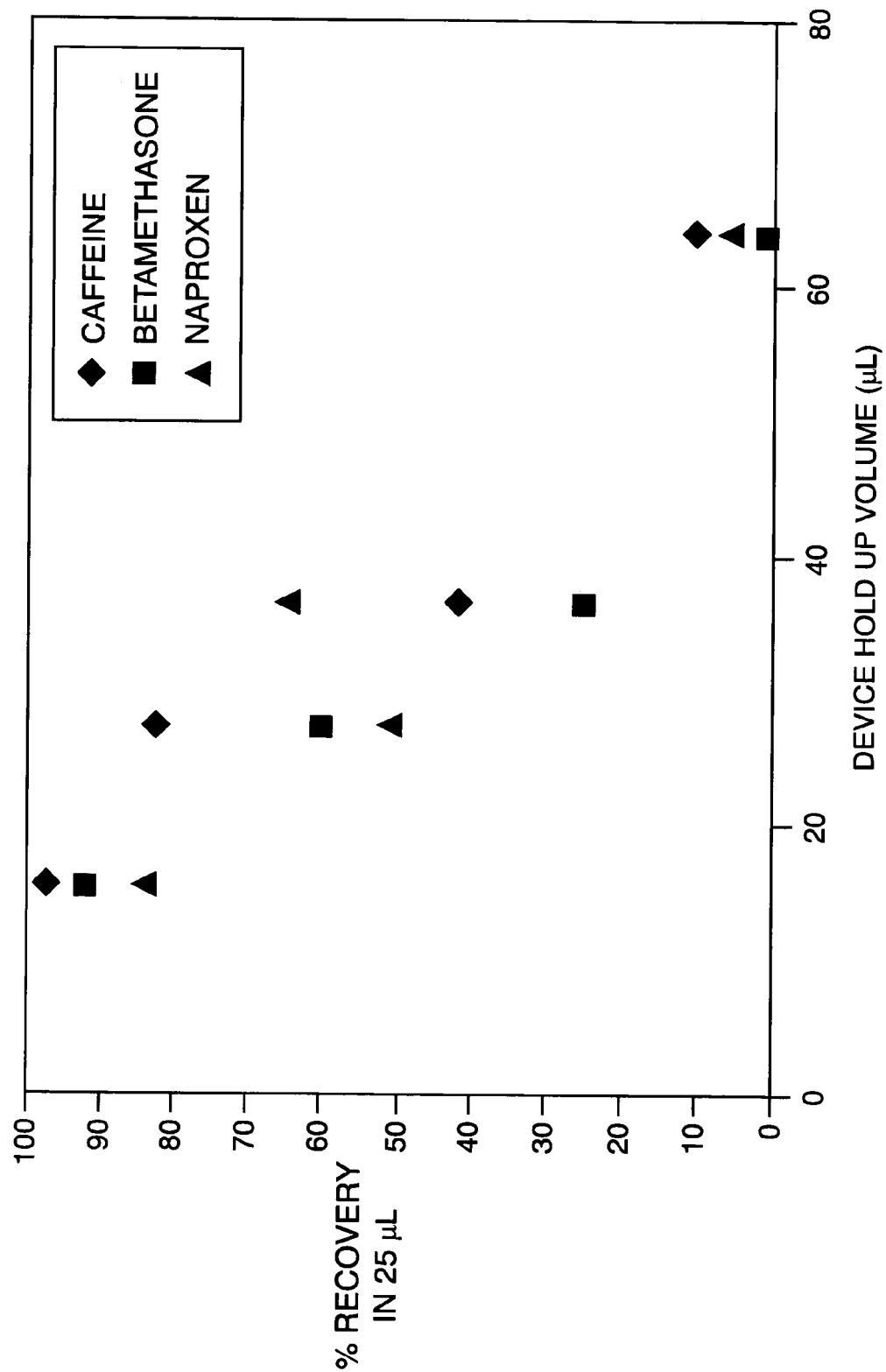
FIG. 4 is a graph illustrating the effect of hold-up volume on recovery in 25 µL elution volumes.

The hold-up volume for each of the devices tested was measured and is shown in Table 5 along with the recoveries for three model compounds. The recoveries for these model compounds are highest for the new tip device due to its low hold-up volume. The recoveries in Table 5 show a trend of lower recoveries for devices with higher hold-up volumes as illustrated in FIG. 4. In FIG. 4, % recovery in 25 μL is plotted against the device hold-up volumes (V) in μL. Diamonds indicate caffeine data, squares indicate betamethasone data and triangles indicate naproxen data

TABLE 5

The Effect of Hold-up Volume on Recovery in 25 μL Elution Volumes

|  | Inventive Device Oasis® HLB 2 mg packed bed | Oasis® HLB 5 mg Plate packed bed | Ansys® Spec Plus C18 Plate glass fiber disk | 3M Empore™ Universal Resisn Plate teflon disk |
|---|---|---|---|---|
|  | Elution Volume | | | |
|  | 25.0 μL | 25.0 μL | 25.0 μL | 25.0 μL |
| caffeine | 97.0 | 82.3 | 41.3 | 9.8 |
| betamethasone | 91.5 | 59.9 | 24.3 | 0.7 |
| naproxen | 84.1 | 50.8 | 64.4 | 5.3 |
| Device hold up volume (μL) | 16.0 | 28.0 | 36.0 | 64.0 |

Packed beds having a bed height to top diameter ratio of <0.23 are not able to efficiently retain or elute compounds due to imperfections in the packed bed. Simply going to a 2 mg amount of sorbent in the existing Oasis® HLB plate will not provide a result comparable to those obtained on the new device containing 2 mg. This is illustrated with the data in Table 6 showing lower recoveries for all but the most non-polar compounds on the plate containing 2 mg of sorbent compared to the plate containing 5 mg of sorbent. Table 7 shows that the RSDs are worse on the 2 mg plate compared to the 5 mg plate.

TABLE 6

Effect of Bed Height to Top Diameter Ratio on Recovery in 25 μL

|  | Inventive Device Oasis® HLB 2 mg packed bed | Oasis® HLB 2 mg Plate packed bed | Oasis® HLB 5 mg Plate packed bed |
|---|---|---|---|
|  | Elution Volume | | |
|  | 25 μL | 25 μL | 25 μL |
| N-acetyl procainamide | 95.6 | 53.3* | 85.8 |
| practolol | 92.8 | 48.9* | 83.6 |
| acetaminophen | 93.1 | 49.5* | 77.5 |
| caffeine | 97.0 | 59.4* | 82.3 |
| propranolol | 89.3 | 62.2* | 70.2 |
| amitriptyline | 83.6 | 60.3* | 59.1 |
| betamethasone | 91.5 | 66.5* | 59.9 |
| naproxen | 84.1 | 53.7* | 50.8 |
| Bed height to top diameter ratio | 0.97 | 0.092 | 0.23 |

*Breakthrough in the load and wash was 14–43%.

All others show <5% breakthrough.

TABLE 7

Effect of Bed Height to Top Diameter on Recovery RSDs in 25 μL

|  | Inventive Device Oasis® HLB 2 mg packed bed | Oasis® HLB 2 mg Plate packed bed | Oasis® HLB 5 mg Plate packed bed |
|---|---|---|---|
|  | Elution Volume | | |
|  | 25 μL | 25 μL | 25 μL |
| N-acetyl procainamide | 0.9 | 44.6 | 5.0 |
| Practolol | 1.2 | 46.5 | 6.1 |
| acetaminophen | 1.6 | 42.0 | 6.4 |
| Caffeine | 1.7 | 38.0 | 4.6 |
| propranolol | 1.6 | 29.2 | 6.7 |
| amitriptyline | 4.0 | 22.7 | 7.6 |
| betamethasone | 2.5 | 17.5 | 8.6 |
| Naproxen | 2.5 | 20.5 | 10.5 |
| Bed height to top diameter | 0.97 | 0.092 | 0.23 |

Example 6

Devices similar to those shown in FIG. 1 were manually packed using 1.0±0.05 mg of 30 μm Oasis® HLB (Waters Corporation) contained between two polyethylene spherical frits: a 0.035" spherical frit at the bottom of the bed and a 0.055" spherical frit at the top of the bed. Sodium chloride, Angiotensin II, and p-toluamide were obtained from Sigma-Aldrich. Triethylamine (TEA), glacial acetic acid, trifluoroacetic acid (TFA), and HPLC grade acetonitrile were obtained from J. T. Baker. The 15-mer oligodeoxythymidine (15-mer oligo T) was obtained from Midland Certified Reagent Company (Midland Tex.). The 0.1 M triethylammonium acetate (TEAAc) was prepared by adding 2.21 mL of glacial acid and 5.58 mL of triethylamine to 350 mL of H2O. The solution was mixed, adjusted to a volume of 400 mL and pH adjusted to pH 7 using acetic acid. The 0.24% TFA, and 50% acetronitrile were prepared by volume. The 50 mM NaCl was prepared by adding 0.0584 grams of NaCl to 1 liter of H2O. The 0.1 M TEAAc with 50 mM NaCl was prepared by adding 2.21 mL of glacial acid and 5.58 mL of triethylamine to 350 mL of 50 mM NaCl. The solution was mixed, adjusted to a volume of 400 mL with 50 mM NaCl and pH adjusted to pH 7 using acetic acid. The 60 μL DNA load sample contained 1 μg of 15-mer oligo T and 1 μg of p-toluamide in the 0.1 M TEAAc buffer with 50 mM NaCl. The 60 μL peptide load sample contained 1 μg of Angiotensin II and 1 μg of p-toluamide in the 0.24% TFA. All solutions were drawn through the tips using a vacuum of <5"Hg.

DNA Desalting Method:
1. Condition each tip (n=3) with 60 μL of acetonitrile followed by 60 μL of 0.1 M TEAAc buffer
2. Load 60 μL/tip of the DNA sample
3. Wash with 60 μL/tip of the 0.1 M TEAAc buffer followed by 60 μL/tip of $H_2O$
4. Elute each tip with 10 μL of 50% acetonitrile in $H_2O$ Peptide Method:
1. Condition each tip (n=4) with 60 μL of acetonitrile followed by 60 μL of 0.24% TFA
2. Load 60 μL/tip of the peptide sample
3. Wash with 20 μL of the 0.24% TFA followed by 20 μL of $H_2O$
4. Elute each tip with 10 μL of 50% acetonitrile in $H_2O$ The DNA desalting and peptide recovery results are presented in Table 8. The results in Table 8 show that excellent recoveries for small molecules (ie p-toluamide), biopolymers (15-mer oligo T) and peptides can be obtained in 10 μL elution volumes.

TABLE 8

Recoveries and RSDs for 15-mer oligo T, Angiotensin II, and p-Toluamide

|  | % Recovery | % RSD |
|---|---|---|
| DNA Method | | |
| 15-mer oligo T | 88.2 | 2.3 |
| p-Toluamide | 93.3 | 4.8 |
| Peptide Method | | |
| Angiotensin II | 101.6 | 1.2 |
| p-Toluamide | 96.7 | 4.7 |

According, it should be readily appreciated that the device and method of the present invention has many practical applications. Additionally, although the preferred embodiments have been illustrated and described, it will be obvious to those skilled in the art that various modifications can be made without departing from the spirit and scope of this invention. Such modifications are to be considered as included in the following claims.

What is claimed:

1. A method of providing for a range of sorbent masses within a solid phase extraction device comprising:
   providing an solid phase extraction device comprising a reservoir with an opening for receiving fluids; a well comprising an internally tapered wall, the well having a wider interior diameter at a first end closest to the reservoir than at a second end close to an exit spout, the well for conducting an extraction; an exit spout at the second end of the well for discharging fluids; a first filter press sealed between the internally tapered walls of the well for retaining insoluble components of the fluids; a second filter having a smaller diameter than the first filter press-sealed between the internally tapered walls of the well spaced apart and toward the exit spout from the first filter; a quantity of sorbent particles partial filing the volume in the well between the first and second filters; and a void volume between the quantity of sorbent particles and the first filter for separating the quantity of sorbent particles from the first filter; and
   adjusting the filter diameters whereby the filters settle in different positions within the tapered well.

2. The method of providing for a range of sorbent masses within a solid phase extraction device as in claim 1 further comprising:
   the reservoir and well in a multi-well array.

3. A method of making an extraction device comprising:
   providing a housing having a reservoir with an opening for receiving fluids and a well having a wall that tapers at an included angle of between 1 and 30° with an exit spout at a narrow end of the well and an opening at a wide end of the well, the well including a lower diameter of an inverted conical frustum that provides a specified aspect ratio when a selected volume of sorbent particles are placed in the well at that lower diameter;
   placing a smaller spherical filter with a diameter equal to the lower diameter in the well;
   placing the selected volume of sorbent particles in the well; and
   placing a larger spherical filter, with a diameter sufficiently large to position it above a void volume above the volume of sorbent particles, in the well.

4. The method of claim 3 wherein after the smaller spherical filter is placed in the well, it is pressed in place.

5. The method of claim 3 wherein after the larger spherical filter is placed in the well, it is pressed in place.

6. The method of claim 3 wherein the volume of sorbent particles is placed in the well by pouring a slurry containing the volume of sorbent particles into the well and allowing the liquid to exit through the exit spout.

7. The method of claim 3 wherein the filters are placed in the well by dropping them into the well and allowing them to find a seating point.

8. A method of making an extraction device comprising:
   providing a housing having a reservoir with an opening for receiving fluids and a well having a wall that tapers at an included angle of between 1 and 30° with an exit spout at a narrow end of the well and an opening at a wide end of the well, the well including the lower diameter of an inverted conical frustum that provides a specified aspect ratio when a selected volume of sorbent particles are placed in the well at that lower diameter;
   press sealing a spherical filter with a diameter equal to the lower diameter in the well;
   placing the volume of sorbent particles in the well; and
   press sealing a second spherical filter, with a diameter sufficiently large to position it above a void volume above the volume of sorbent particles, in the well.

* * * * *